(12) United States Patent
Szames et al.

(10) Patent No.: US 6,508,792 B2
(45) Date of Patent: Jan. 21, 2003

(54) DISCOID AND ELASTIC VALVE TO PRODUCE A HERMETIC CLOSURE INSIDE PRE-FILLED SYRINGES

(76) Inventors: Leonardo Szames, 1641 Tabaré Street, Buenos Aires (AR); Saúl Moreno, 1641 Tabaré Street, Buenos Aires (AR); Jaime Luis Szapiro, 1641 Tabaré Street, Buenos Aires (AR)

( * ) Notice: Subject to any disclaimer, the term of this patent is extended or adjusted under 35 U.S.C. 154(b) by 0 days.

(21) Appl. No.: 09/822,137

(22) Filed: Mar. 30, 2001

(65) Prior Publication Data

US 2001/0029355 A1 Oct. 11, 2001

(30) Foreign Application Priority Data

Apr. 5, 2000 (AR) .................................... 00 01 01565

(51) Int. Cl.⁷ .............................................. A61M 5/315
(52) U.S. Cl. ...................... 604/237; 604/218; 604/236
(58) Field of Search ................................ 604/181, 187, 604/218, 236, 237

(56) References Cited

U.S. PATENT DOCUMENTS

| | | | | |
|---|---|---|---|---|
| 3,373,743 A | * | 3/1968 | Saffir | 604/237 |
| 4,112,924 A | * | 9/1978 | Ferrara et al. | 604/237 |
| 5,478,323 A | * | 12/1995 | Westwood et al. | 604/237 X |
| 5,626,567 A | * | 5/1997 | Gmeiner | 604/236 |

* cited by examiner

Primary Examiner—Steven J. Ganey
(74) Attorney, Agent, or Firm—Bachman & LaPointe, P.C.

(57) ABSTRACT

A discoid and elastic valve is designed to block up the neck of the syringe from inside, in order to close the communication between the syringe's internal main body, where the liquid is, and the needle which is connected in the syringe neck through its plugging cone.

7 Claims, 5 Drawing Sheets

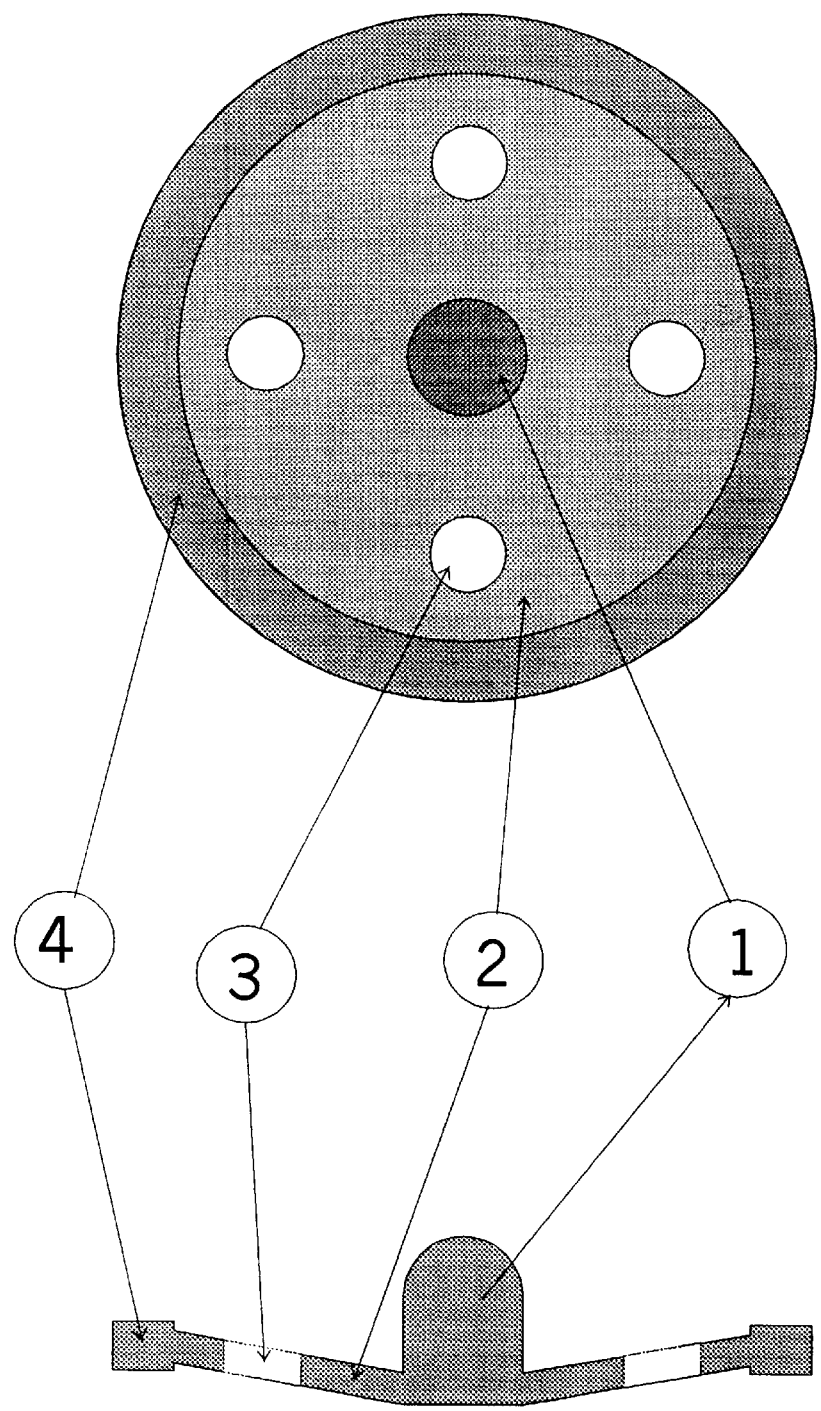

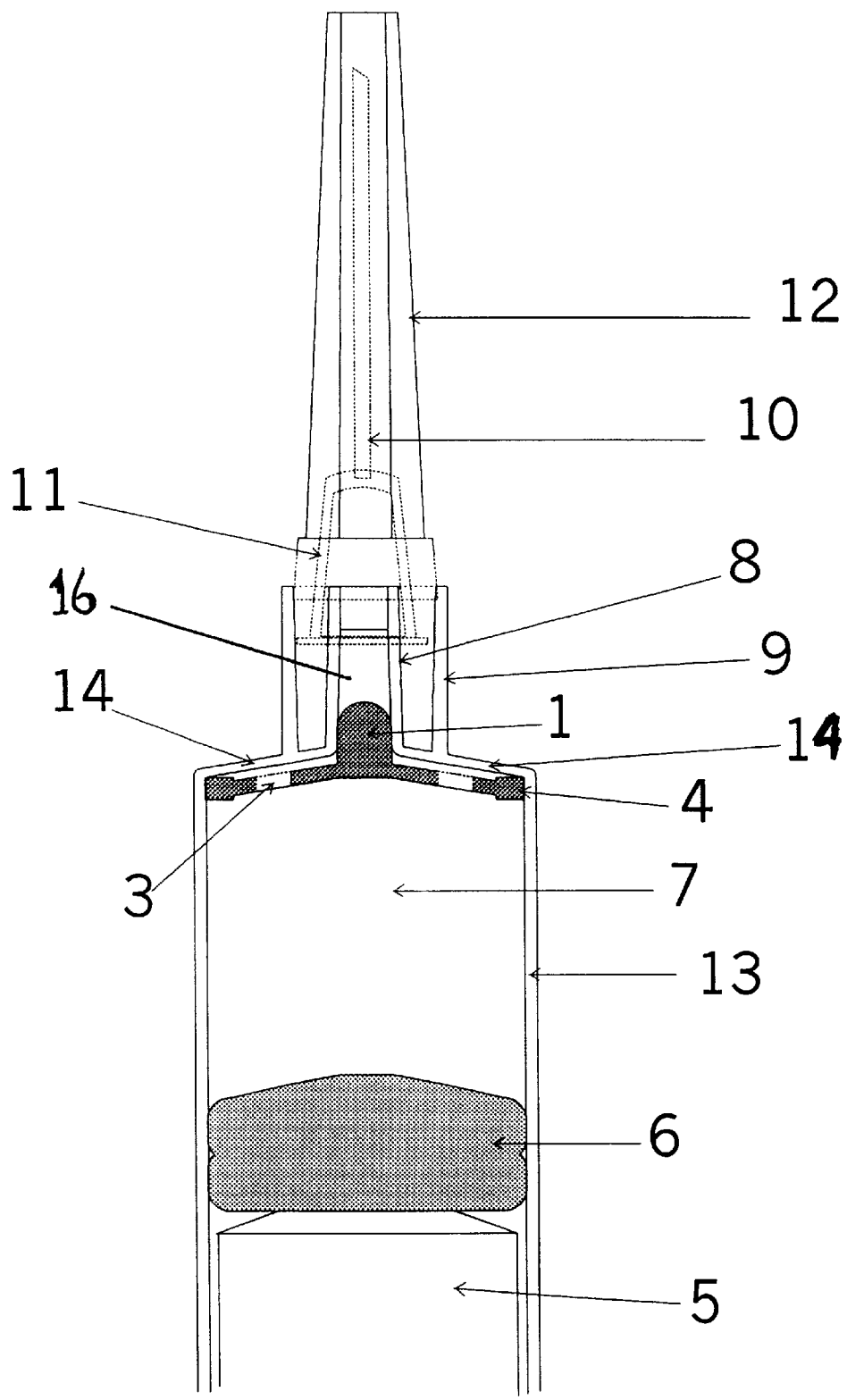

DISCOID AND ELASTIC VALVE TO PRODUCE A HERMETIC CLOSURE INSIDE PRE-FILLED SYRINGES

BACKGROUND OF THE INVENTION

The present invention is drawn to pre-filled syringes and, more particularly, a discoid and elastic valve to produce a hermetic closure inside a pre-filled syringe which keeps the liquid content to be injected totally isolated, in order to prohibit the liquid from coming in contact with the needle or the external air. More specifically, a discoid and elastic valve is designed to block up the neck of the syringe from inside, in order to close the communication between the syringe's internal main body, where the liquid is, and the needle which is connected in the syringe neck through its plugging cone.

The characteristic feature of known pre-filled syringes is that they have a cylindrical and hollow main body, with a front section where a communication neck with the injection needle is formed, while inside is a manually movable plunger which extends outward from the back of the main body which is open. All of these known syringes have an inner chamber formed inside the main body, constituting the temporary location of the liquid to be injected. This inner chamber is defined by the cylindrical wall of the main body, the above mentioned front neck where the needle and the active head of the manually movable plunger.

Argentine Patent No. 250,277 discloses a syringe which supports a very special valve plug whose function is to keep the liquid isolated inside of syringe body thus avoiding contact with the needle until the injection is performed. Thus, during the placement of the needle and coupling it to the plugging cone or syringe neck and withdrawal of the protecting sheath to perform the injection, the liquid is kept isolated inside the main body of the syringe, ensuring that these coupling and uncoupling actions do not cause some unwanted loss or spilling. The plug is specially designed to be placed in the neck occluding the same from the outlet mouth. It is important to point out that the plug of the mentioned Patent No. 250,277 is specially designed for the mouth of the syringe neck that faces the injection needle. Due to its special shape the same releases the liquid only when hydraulic pressure is produced from the plunger towards the syringe. This pressure partially removes the plug and the liquid flows.

SUMMARY OF THE INVENTION

The discoid valve of the present invention is also specially designed to isolate the liquid contained in a pre-filled syringe, avoiding its contact with the needle; however, it clearly differs from the cited prior art due to the fact that it works operatively in a different way.

The valve of the present invention is located inside the main body to perform the closing action at the inlet of the communication duct that defines the neck of the syringe. The valve of the present invention has a coaxial stub that fits in the inner part of the syringe neck closing it and forming a hermetic chamber that contains the liquid to be injected. This new arrangement ensures the impossibility of unwanted losses of liquid, with the additional feature that, being inside the syringe body, every manipulation that may be performed during the couplings and uncoupling of the injection needle, as well as its respective protection sheath, may never lead to leakage. Likewise, if the plunger is accidentally pushed in an injection action, the seal will be greater.

The new functional concept incorporated with the invented valve is that it is necessary the plunger move in a direction opposite to the injection direction in order to provide a free flow of the liquid to the needle. When moved as described above, the stub is removed from its sealing location and the valve withdraws itself thereby allowing the passage of liquid.

This action, which is not possible with other plugs, is very important in that the action necessary for the release of the closing stub, allows one to know that the needle is inserted correctly. As it is known, if the needle is inserted in a vein, the sucking action, causes the entrance of blood in the syringe which is desirable and necessary evidence of proper location.

Accordingly, it is the principle object of the present invention to provide a discoid and elastic valve to produce a hermetic closure inside pre-filled syringes suitable to be placed inside the syringe body, occluding the communication passage towards the injection needle fitted on the neck of these, which consists in a single body that comprises a cylindrical stub that projects itself perpendicularly from a flat and elastic central portion (base) of circular shape, which includes a series of holes neatly distributed therein and is limited by a perimetrical ring that fits tightly on the inner face or the cylindrical wall of the syringe.

Another characteristic of the value is that the cylindrical stub projects from the center of a flat and elastic base and the holes are neatly distributed in a circular manner on the flat base. It should also be noted that the perimetrical ring is circumferential and thicker than the elastic base (central portion).

BRIEF DESCRIPTION OF THE DRAWINGS

A preferred performing example, which is illustrated, is merely explicative and illustrative intention of the basis conception in which the invention is based.

FIG. 1 is a top view that represents a discoid valve like the one supported in this document.

FIG. 2 is a cross-section of the same discoid valve represented en the previous figure.

FIG. 3 is a vertical section of a syringe including, inside its main body, a discoid valve, according to this invention, adopting the closing position.

It should be explained that, in every figure, same reference numbers correspond to same or equivalent parts or constitutive elements of the group, according to the example chosen for the present explanation of the invented discoid valve.

DETAILED DESCRIPTION

Figure 4:
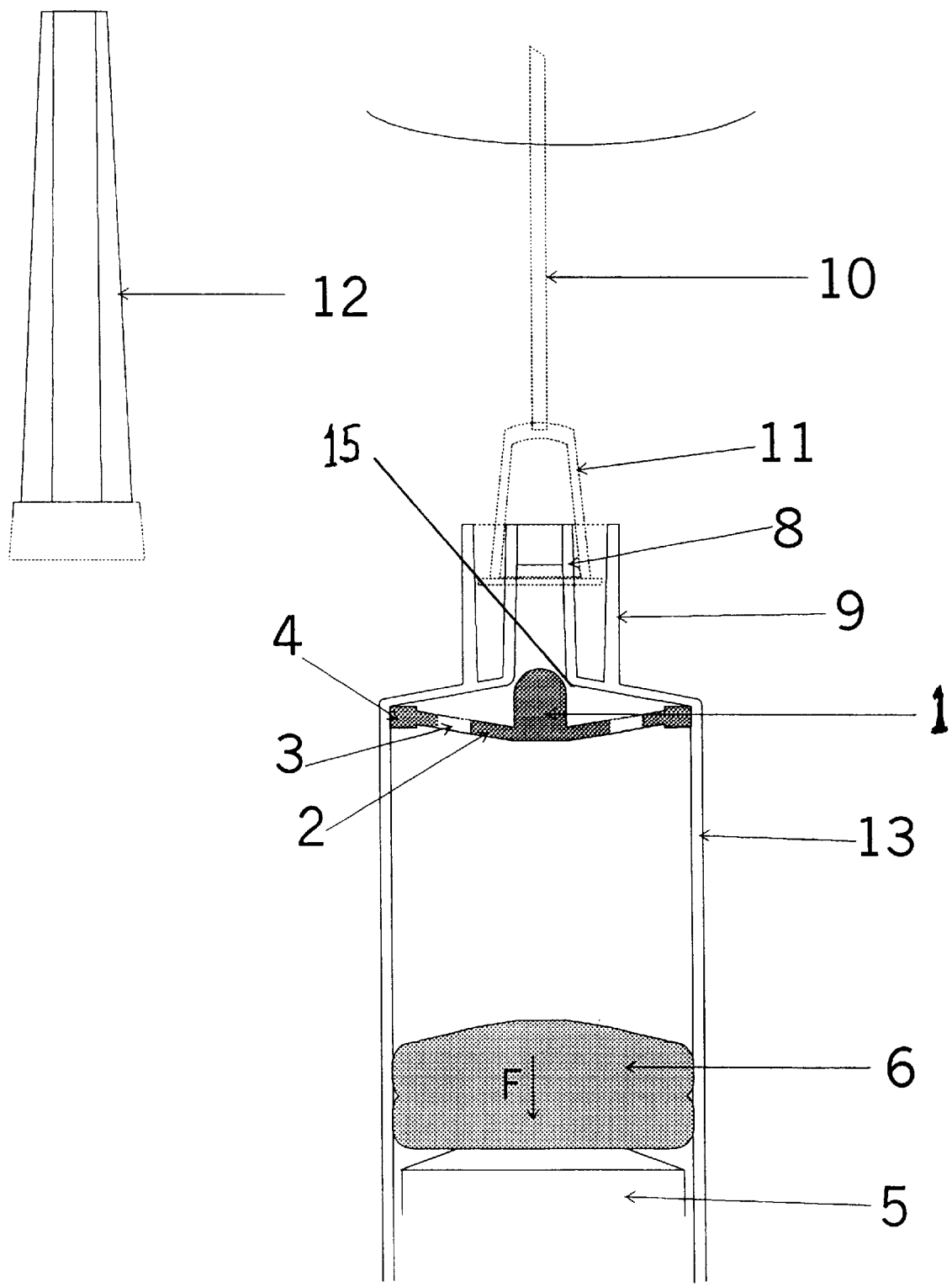
FIG. 4 is a vertical section of a syringe that includes the invented discoid valve, in this case in an open disposition to allow the passage of liquid.

As it may be seen in FIGS. 1 and 2, the discoid and elastic valve to produce a hermetic closure inside pre-filled syringes to which this invention refers, is a single body that comprises a central stub 1 with a cylindrical shape and a cap-shaped higher base that projects from a flat and central portion 2 with a circular form in which a series of properly distributed holes are defined 3. This central portion 2 is limited by a circumferential ring 4 that acts as perimetric border of the valve.

If we now refer to FIGS. 3 to 6 it is possible to appreciate that this discoid valve is specially designed to operate in pre-filled syringes such as the ones described, which comprise a syringe body 13 with a cylindrical shape, inside of which the plunger is placed 5 that is manually movable and has its active head 6 which is the one that determines the bottom of a chamber of variable volume 7 that is where the liquid product to be supplied is located.

The above mentioned internal chamber 7 is defined by the cylindrical wall of the main body 13, the cited active head 6 and a front base where the neck originates 8 that together with the wall 9 define the "plugging cone" or coupling means for the injection needle.

In these same figures, with the reference 10 the mentioned needle that, through the middle 11 couples with the syringe assembling in the mentioned "plugging cone" 8/9 is represented. The sheath 12 that also couples the mentioned plugging cone 8/9, protects this whole group.

Thus the group is constituted, and as FIG. 3 shows, the invented valve is suitable to be placed on the base 14 of the syringe body in a way that the stub 1 is received in outlet 15 and clearly closes the communication passage 16 towards the needle 10. In this way a hermetic chamber is formed 7 where the liquid to be injected is located.

It is noted that the way the valve of this invention is placed, it is impossible to have spilling of the contained liquid, also during the movements and manipulations that occur during the placement of the needle 10 and the placement or removal of its protective sheath 12. In fact, the valve prevents any possibility of liquid loss.

Observing now FIG. 4, it can be appreciated that, once the protective sheath is removed 12 and with the needle in place 11 in use position, the operator can move the plunger in the direction indicated with the reference F. The effect produced consists in the deformation of the elastic central portion 2 at the junction with ring and until the stub 1 releases the passage (through the inside of the neck 8) towards the injection needle. The liquid located in chamber 7 goes through the mentioned holes 3 and in this way is led through the inside of the neck 8 towards the needle.

The periphery of the valve always remains in the same position because its circumferential ring fits tightly in the internal face of the cylindrical wall of the syringe body, with a higher adjusting pressure than the one required to bend the central portion 2 and deform it in the direction and sense F in order to remove the stub 1 from its closing position.

As FIG. 4 shows, if the needle 12 is inserted in a vein, such releasing action by elastic deformation of the base central portion 2 will cause the entrance of blood in the syringe, which is a necessary and common evidence every time one tries to inject a liquid, since the injection, could be intravenous or not, is suitable to ensure that the destination of the liquid is the one wanted.

Figure 5:
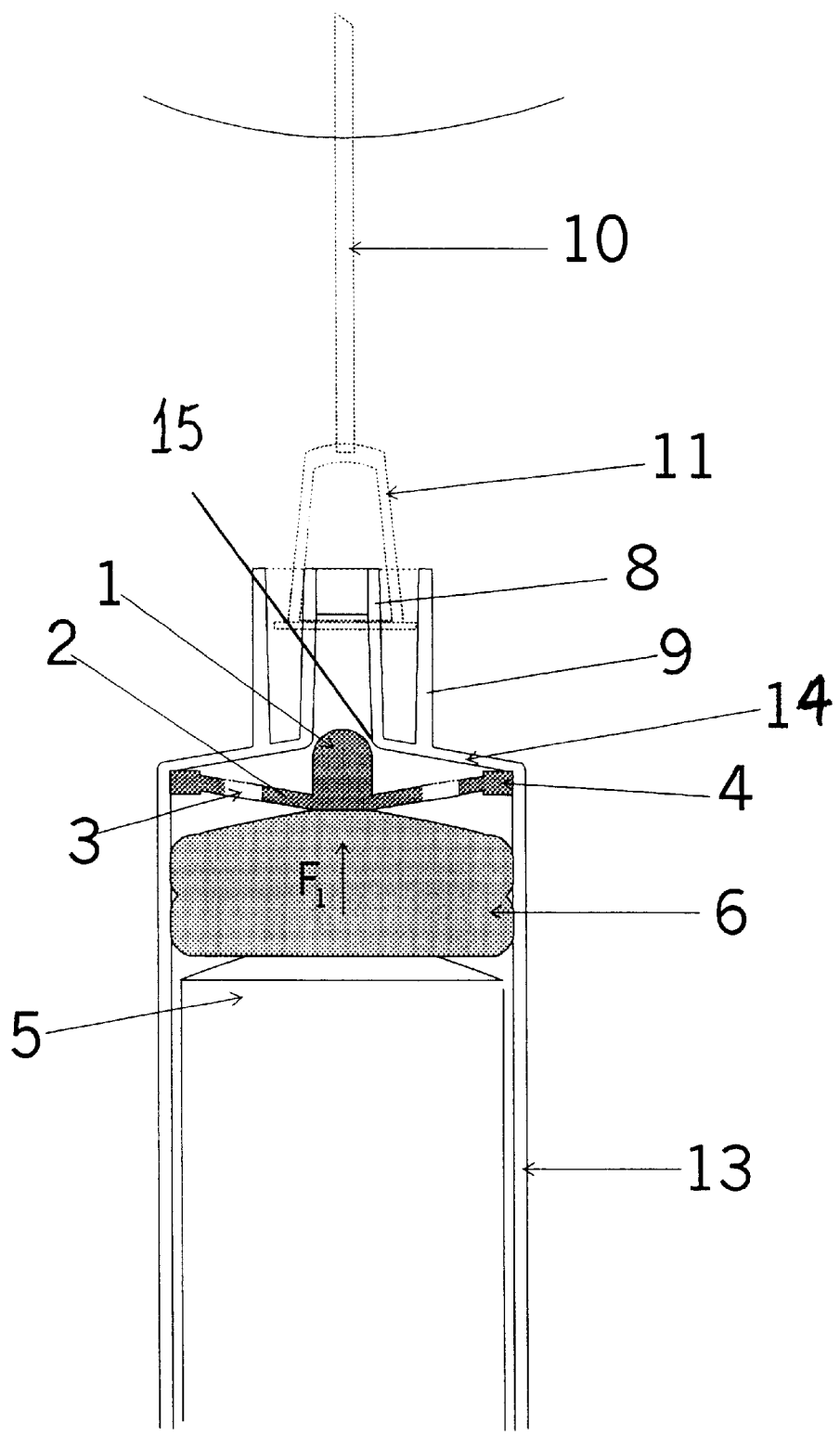
FIG. 5 is also a vertical section that shows the disposition of the plunger when it has moved in the direction of the injection, evacuating much of the liquid contained in the syringe.
Figure 6:
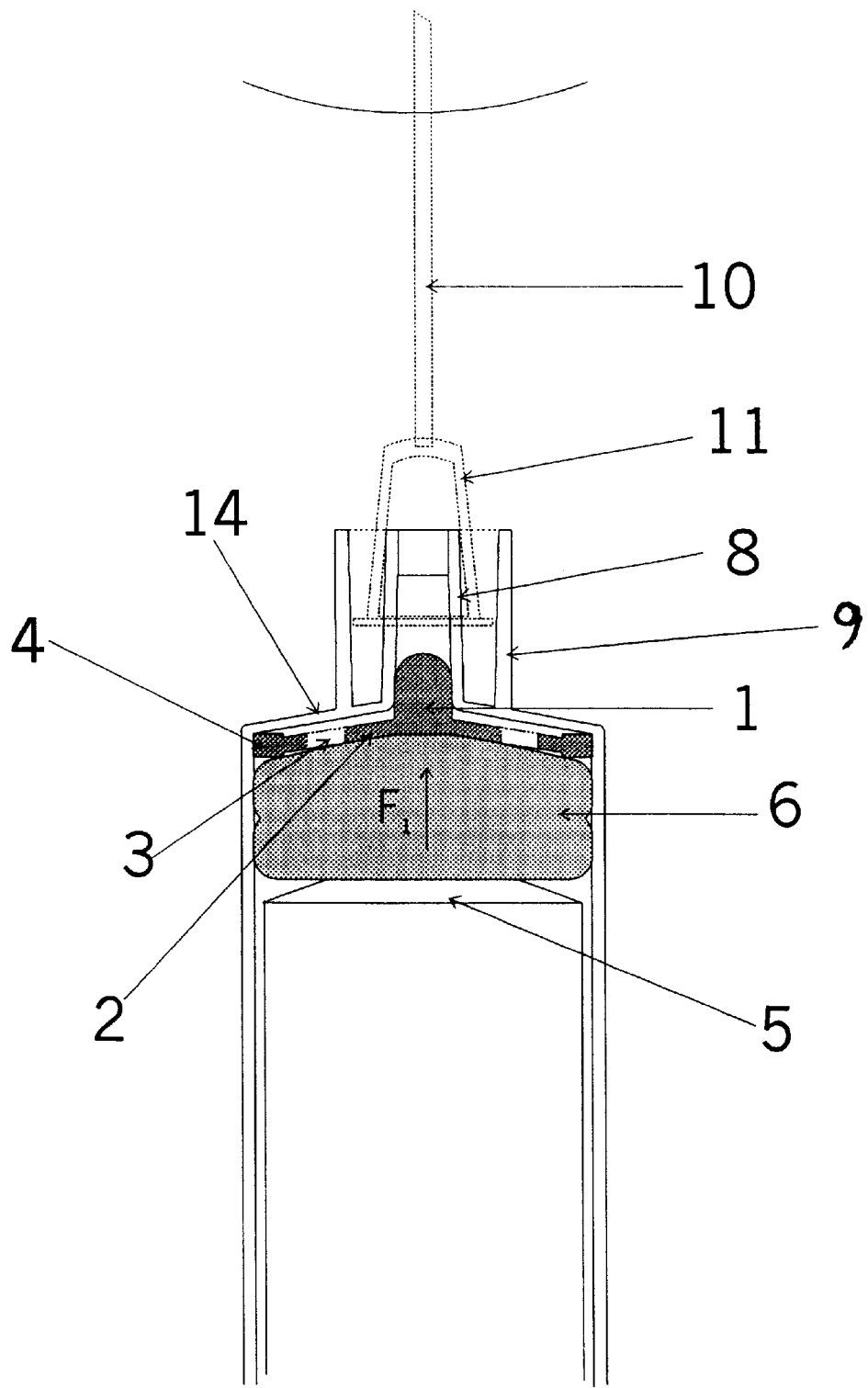
FIG. 6 is also a vertical section where the disposition of the invented valve after injecting all the liquid is shown.

If we observe now FIGS. 5 and 6 it may be appreciated that with the movement of the plunger in the direction F1 it is possible to remove the whole liquid contained inside the chamber 7 since the same flows through the holes 3 until the valve adopts the initial position, that is to say, with the plug 1 closing the neck passage 8. The control portion 2 "snaps" between the closed position and open position at the junction with ring and remains in the open position until the plunger 5 or active head 6.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A prefilled syringe having a cylindrical wall connected to a base and a moveable plunger which together with the cylindrical wall and base define an internal chamber for a liquid product to be dispensed, the base is provided with an outlet communicating with a passage for feed product from the internal chamber through the passage and to a needle upon movement of the plunger toward the base, the improvement which comprises a discoid and elastic valve positioned within the internal chamber and moveable between a first position where the valve seals the outlet and to a second position where the outlet is opened, wherein the valve has a peripheral portion and a central portion, the central portion being movable with respect to the peripheral portion and wherein the central portion is provided with closure element received in the outlet for sealing the outlet when the valve is in the first position.

2. A syringe according to claim 1, wherein the central portion includes openings for communicating the internal chamber with the outlet and passage when the valve is in the second position.

3. A syringe according to claim 2, wherein the openings are distributed around the closure element.

4. A syringe according to claim 1, wherein the peripheral portion is rigid.

5. A prefilled syringe having a cylindrical wall connected to a base and a moveable plunger which together with the cylindrical wall and base define an internal chamber for a liquid product to be dispensed, the base is provided with an outlet communicating with a passage for feed product from the internal chamber through the passage and to a needle upon movement of the plunger toward the base, the improvement which comprises a discoid and elastic valve positioned within the internal chamber and moveable between a first position where the valve seals the outlet and to a second position where the outlet is opened, wherein the valve has a peripheral portion and a central portion, the central portion being movable with respect to the peripheral portion and wherein the peripheral portion is rigid.

6. A syringe according to claim 5, wherein the central portion is provided with closure element received in the outlet for sealing the outlet when the valve is in the first position.

7. A syringe according to claim 5, wherein the peripheral portion is thicker than the central portion.

* * * * *